US012559630B2

(12) United States Patent
Suzuki et al.

(10) Patent No.: US 12,559,630 B2
(45) Date of Patent: Feb. 24, 2026

(54) COATED PIGMENT

(71) Applicant: TOYO ALUMINIUM KABUSHIKI KAISHA, Osaka (JP)

(72) Inventors: Sachiko Suzuki, Osaka (JP); Hideaki Minamiyama, Osaka (JP)

(73) Assignee: TOYO ALUMINIUM KABUSHIKI KAISHA, Osaka (JP)

( * ) Notice: Subject to any disclaimer, the term of this patent is extended or adjusted under 35 U.S.C. 154(b) by 438 days.

(21) Appl. No.: 18/015,574

(22) PCT Filed: Jul. 7, 2021

(86) PCT No.: PCT/IB2021/056066
§ 371 (c)(1),
(2) Date: Jan. 11, 2023

(87) PCT Pub. No.: WO2022/013681
PCT Pub. Date: Jan. 20, 2022

(65) Prior Publication Data
US 2023/0250294 A1 Aug. 10, 2023

(30) Foreign Application Priority Data
Jul. 14, 2020 (JP) ................................ 2020-120328

(51) Int. Cl.
*C09C 3/06* (2006.01)
*A61K 8/19* (2006.01)

(52) U.S. Cl.
CPC ................ *C09C 3/063* (2013.01); *A61K 8/19* (2013.01)

(58) Field of Classification Search
CPC ............................. C09C 3/063; C09C 1/0015
See application file for complete search history.

(56) References Cited

U.S. PATENT DOCUMENTS 4,177,321 A * 12/1979 Nishizawa .......... H01L 21/0242
428/428
5,364,467 A * 11/1994 Schmid ................. C09C 1/0015
106/404
2007/0032573 A1 2/2007 Yanagase et al.
2012/0091702 A1 4/2012 Shimizu et al.
2013/0257035 A1 10/2013 Shimizu et al.
2015/0005393 A1 1/2015 Abiko et al.
2017/0348202 A1* 12/2017 Grüner ..................... A61Q 3/02

FOREIGN PATENT DOCUMENTS

| CN | 101445674 | 6/2009 | |
| CN | 102803400 | 11/2012 | |
| CN | 103249783 | 8/2013 | |
| EP | 1666541 A1 * | 6/2006 | .......... A61K 8/0262 |
| JP | 61-19666 | 1/1986 | |
| JP | 10-259318 | 9/1998 | |
| JP | 2008-247757 | 10/2008 | |
| JP | 2015-120927 | 7/2015 | |
| JP | 2015-178556 | 10/2015 | |
| WO | 98/41584 | 9/1998 | |
| WO | 2005/028566 | 3/2005 | |

OTHER PUBLICATIONS

International Search Report issued Sep. 14, 2021 in corresponding International (PCT) Patent Application No. PCT/IB2021/056066.
English translation of International Preliminary Report on Patentability issued Jan. 17, 2023 in corresponding International (PCT) Patent Application No. PCT/IB2021/056066.

* cited by examiner

*Primary Examiner* — Pegah Parvini
(74) *Attorney, Agent, or Firm* — Wenderoth, Lind & Ponack, L.L.P.

(57) ABSTRACT

A coated pigment is used which includes a base of which at least the surface is composed of a light-transmitting material; and a magnetite layer coating the base, and having a crystal lattice constant of not less than 8.35 Å. At least one selected from the group consisting of silica, alumina, glass, mica and a resin is usable as the light-transmitting material.

5 Claims, 2 Drawing Sheets
(2 of 2 Drawing Sheet(s) Filed in Color)

COATED PIGMENT

TECHNICAL FIELD

The present invention relates to a coated pigment coated with a magnetite layer.

BACKGROUND ART

As conventional pigments, pigments are known in which a single or composite film composed of silicon oxide, titanium oxide, iron oxide, metal, etc. is formed on the surface of a transparent base material such as mica, alumina or glass, or the surface of an aluminum pigment, thereby providing interference colors.

For example, the below-identified Patent Document 1 discloses a coated pigment in which a ferrite layer is formed on the surface of a light-transmitting base material, or the surface of a metal base material formed with a light-transmitting layer on the surface thereof.

Also, the below-identified Patent Document 2 discloses an orange pearl pigment in which the surface of a flaky substrate is coated with a metal oxide containing iron oxide.

PRIOR ART DOCUMENT(S)

Patent Document(s)

Patent Document 1: Japanese Unexamined Patent Application Publication No. 2015-178556

Patent Document 2: Japanese Unexamined Patent Application Publication No. H10-259318

SUMMARY OF THE INVENTION

Problems to be Solved by the Invention

However, it is hard to say that the pigment of Patent Document 1 has sufficient chroma or color developing properties. The color tone obtained in the pigment of Patent Document 2 is limited to red-based colors or yellow-based colors.

Therefore, it is an object of the present invention to provide a pigment having high chroma and interference colors of various color tones.

Means for Solving the Problems

As a result of diligent study in view of the above situation, the inventors of the present application discovered that the above problems can be solved by coating, with a magnetite layer, a base of which at least the surface is composed of a light transmitting material, and controlling the magnetite layer to a predetermined crystal structure, and they reached the present invention.

That is, the present invention is summarized in the following [1] to [8]:

[1] A coated pigment comprising: a base of which at least a surface is composed of a light-transmitting material; and a magnetite layer coating the base, and having a crystal lattice constant of not less than 8.35 Å.

[2] The coated pigment according to [1], wherein the light-transmitting material is at least one selected from the group consisting of silica, alumina, glass, mica and a resin.

[3] The coated pigment according to [1] or [2], wherein the base comprises metal flakes coated with the light-transmitting material.

[4] The coated pigment according to [3], wherein the metal flakes are composed of at least one selected from the group consisting of aluminum, copper, nickel, tin, titanium, zinc, an alloy containing any one or more of these metals, and a stainless steel.

[5] The coated pigment according to any one of [1] to [4], further comprising, on the magnetite layer, a protective layer composed of any one of a metal oxide, a metal hydroxide, a metal oxide hydrate, a resin and a combination thereof.

[6] A resin composition containing the coated pigments according to any one of [1.] to [5].

[7] A coated object comprising a base object and the resin composition according to [6] coating the base object.

[8] A cosmetic material containing the coated pigments according to any one of [1] to [5].

Effects of the Invention

The coated pigment of the present invention not only has high chroma and color developing properties, but also can develop various interference colors such as red-based colors, blue-based colors and yellow-based colors to green-based colors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
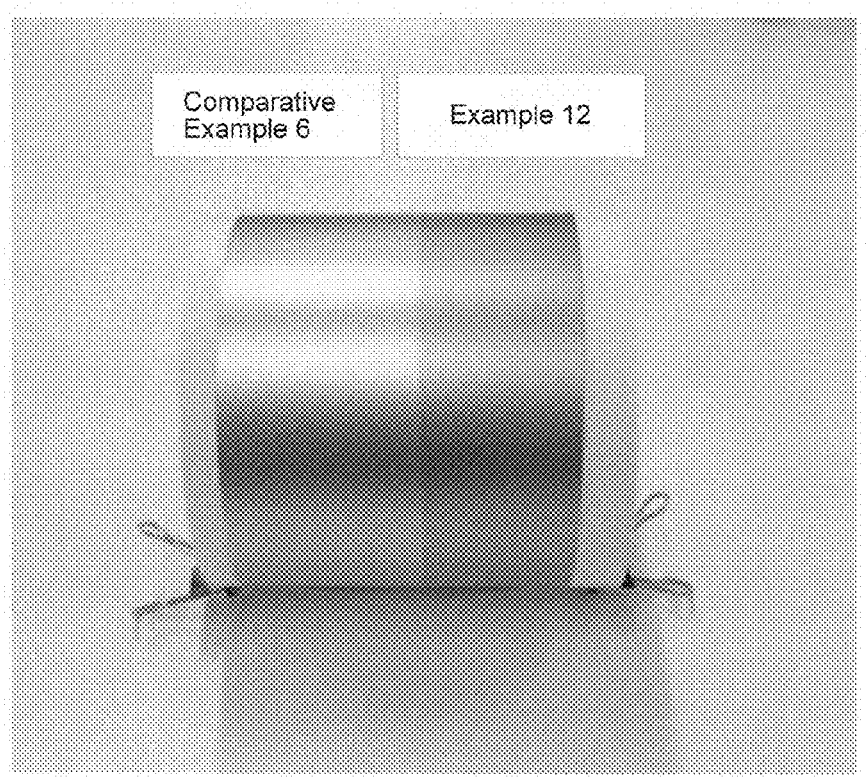
FIG. 1 is a photograph of a sheet which is, after applying thereto coated pigments obtained in Example 12 and coated pigments obtained in Comparative Example 16, rolled into a cylindrical shape.

An embodiment of the present invention is described below in detail.

The present invention is directed to a coated pigment comprising a base of which at least the surface is formed of a light-transmitting material; and a magnetite layer coating the base, the coated pigment having interference colors.

Base

The base of the present invention forms a core of the coated pigment according to the present invention, and at least the surface of the base is formed of a light-transmitting material. As long as at least the surface of the base is composed of a light-transmitting material, the entire base may be formed of the light-transmitting material, or, a core material composed of another material may be coated with the light-transmitting material.

The volume average particle diameter ($D_{50}$) of the base is freely selectable provided that the particle diameter of the coated pigment of the present invention, described later, is achievable, and is preferably 0.5 μm or more and 200 μm or less in that, within this range, the base can be satisfactorily coated with the magnetite layer. If less than 0.5 μm, since the specific surface area of the base is large, it is difficult to sufficiently deposit the magnetite layer on the base. On the other hand, if more than 200 μm, since the specific surface area of the base is small, and the probability of contact of the base with the coating magnetite particles decreases, it is difficult to coat the base with the magnetite layer satisfactorily.

The base is preferably composed of particles or flakes, and particularly preferably flakes.

If the base is a light-transmitting base composed only of the light-transmitting material, a known one is usable without any particular limitation as the light-transmitting base. However, a light-transmitting base composed of silica, alumina, glass, mica, a resin, or a composite of these can be suitably used due to their high light-transmitting properties.

Also, since the light-transmitting base per se is an interference layer, if the light-transmitting base is composed of particles or flakes, the light-transmitting base desirably has a uniform thickness.

Also, if the base comprises a core material and a light-transmitting material coating the surface of the core material, and the core material and the light-transmitting material are different materials, the core material is not particularly limited, and may be a light-transmitting material different from the light-transmitting material forming the surface of the core material, or may be an opaque material. Examples of the opaque material include a metal, a plate-shaped iron oxide, etc. The metal is not particularly limited, and may be any known one. For example, the metal may be aluminum, copper, nickel, tin, titanium, zinc, an alloy containing at least one of these, or a stainless steel.

The light-transmitting material coating the surface of the core material may be the same material as the material used for the above-described light-transmitting base that is composed only of a light transmitting material.

Metal flakes are preferably used as the core material in that a pigment is obtainable which is high particularly in luminance and chroma. As the metal flakes, the use of flakes composed of, of the above-mentioned metals, especially aluminum or an aluminum alloy is suitable, because such flakes are inexpensive and have high luminance.

Also in this case, since the coating layer composed of the light-transmitting material coating the core material is an interference layer that determines the color tone, the coating layer preferably has a uniform thickness. If the light-transmitting layer has a thickness of more than 100 nm, a coated pigment is obtainable which has strong interference colors and high chroma. If the thickness of the layer is further increased, the change of the color tone due to the viewing angle (color travel properties) becomes stronger.

Magnetite Layer

The magnetite layer of the present invention is a layer composed of magnetite and coating the base. If a magnetite layer having a specific crystal lattice constant is used as the magnetite layer coating the base, a coated pigment is obtainable which has higher chroma and color developing properties. Also, by changing the conditions of the components constituting the coated pigment, it is possible to develop interference colors such as red-based colors, blue-based colors and yellow-based colors to green-based colors.

That is, a coated pigment having various interference colors is obtainable.

This is presumably because oxygen atoms have fallen off from the magnetite and oxygen deficiency has occurred, thereby changing the crystal structure. This results in changes in refraction, transmission, etc. of light at the magnetite layer such that the depth and strength of chroma and color developing properties increase, and such that, various interference colors as described above can be developed.

The crystal lattice constant of the magnetite layer needs to be not less than 8.35 Å, and is preferably not less than 8.37 Å. If the crystal lattice constant is less than 8.35 Å, the chroma of the interference colors will decrease, and sufficient color developing properties may not be obtained.

The upper limit of the crystal lattice constant of the magnetite layer is not particularly limited, but is preferably not more than 8.45 Å, and more preferably not more than 8.42 Å. While the upper limit may be more than 8.45 Å, it is difficult to obtain a magnetite layer having a crystal lattice constant of more than 8.45 Å, that is, if more than 8.45 Å, the number of oxygen atoms could decrease markedly such that the magnetite is no longer magnetite.

The average thickness of the magnetite layers of the coated pigments according to the present invention is not particularly limited, but is preferably 10 nm or more and 200 nm or less, and more preferably 20 nm or more and 120 nm or less. Within the latter range, the chroma of the interference colors is particularly good.

[Light-Transmitting Layer of the Base and the Thickness of the Magnetite Layer]

If the base comprises the core material and the light-transmitting material coating the surface of the core material, the color tones of the interference colors change according to the thickness of the magnetite layer, too.

For example, in an arrangement in which, as the base, a metal base composed of aluminum flakes (metal base) formed with a light-transmitting layer composed of silica of about 140 nm is used, if the base is coated with a layer composed magnetite and having a thickness of about 30 nm, a pink-based coated pigment (metallic pigment) having magnetism and high chroma is obtainable, whereas if the base is coated with a layer composed of magnetite and having a thickness of about 100 nm, a coated pigment (metallic pigment) is obtainable of which the color changes from green to purple depending on the angle of observation. This is presumably because thickening the magnetite layer results in a difference in optical path length between the reflected light at the magnetite layer surface and the reflected light at the interface between the magnetite layer and the light-transmitting layer, too.

Protective Layer

The coated pigment of the present invention may further include, if necessary, a protective layer on the surface of the magnetite layer.

The material of the protective layer is not particularly limited provided that it is transparent and does not spoil the color development of the coated pigment. The material of the protective layer can be appropriately selected, according to the purpose, from among, e.g., a metal oxide, a metal hydroxide, a metal oxide hydrate, a resin, a composite of these, etc.

If, for example, the protective layer is composed of a metal oxide, the water resistance improves. If the protective layer is composed of a resin, the adhesion and chemical resistance of a coating film including the coated pigments of the present invention improve.

As the method of forming the protective layer, a known method for coating pigments can be used. Such methods include a method of forming a coating resin layer by radical polymerization in a slurry, and a method of forming a metal oxide layer by the sol-gel method. The protective layer may be formed before or after firing the magnetite layer.

Production of the Coated Pigments

The coated pigments of the present invention can be produced by the following methods.

First, the base can be produced by the following method: If, as the base, a light-transmitting base composed only of the light-transmitting material is used, the light-transmitting base is adjusted to a predetermined size and thickness and used as it is.

If, as the base of each of the coated pigments of the present invention, a base comprising a core material and a light-transmitting material coating the surface of the core material is used, a slurry of the core materials of the coated pigments is prepared by adding, e.g., alcohol, and, by dropping, into the slurry, an alcohol solution containing the components of the raw material of the light-transmitting material, a coating layer of the light-transmitting material is formed on the surface of the core material. Then, by carrying out solid-liquid separation and drying, a base comprising the core material and the light-transmitting material coating the surface of the core material is obtained.

Next, as a method of forming the magnetite layer on the surface of the base of each coated pigment, for example, the following method can be used:

First, a slurry is obtained by dispersing the bases of the coated pigments in water. Then, while stirring the slurry in a deoxidized sealed vessel, an aqueous solution containing $Fe^{2+}$ is gradually added thereto. Since the pH changes during this process, the pH is kept within the range of 6.5 to 14 by a pH adjusting agent, and simultaneously the redox potential of the slurry is kept within the range of about $-160$ mV to $-750$ mV using an oxidant. Due to this, each base can be coated with the magnetite layer. The pH is preferably kept within the range of 6.5 to 11.0, and the redox potential of the slurry is preferably kept within the range of about $-300$ mV to $-500$ mV using an oxidant.

Coated Pigment

The particle diameters of the coated pigments of the present invention produced in this way are not particularly limited, but preferably, though dependent on the intended use, the volume average particle diameter ($D_{50}$) thereof is generally 0.5 μm or more. If this value is less than 0.5 μm, the reflected light on the particle surfaces will increase, thus making it difficult to develop interference colors having high chroma.

For example, when the coated pigments are used in a coating material, if the above value is within the range of 0.5 μm or more and 50 μm or less, the protrusions of coarse particles will not be seen on the surface of the coating film, thus enabling smooth coating.

If the coated pigments are used in printing, the particle diameters are preferably about 20 μm or less to, for example, prevent clogging of a printing plate and ensure concealability in screen printing or gravure printing.

If the coated pigments are used in a cosmetic material or in a resin injection-molded product, large particle diameters are selectable as their particle diameters. By selecting the particle diameters of 50 μm or more, the pigments will provide a shiny granular appearance to the product.

The particle shapes of the coated pigments are not particularly limited, but are preferably flake shapes in that high luminance, chroma and color flop properties are obtainable due to the orientation.

Firing Step

In the present invention, after the magnetite layer is formed, by firing in an inert gas atmosphere, in a reducing gas atmosphere or under a reduced pressure of 50 kPa or less (or in a vacuum), the magnetite layer changes into a magnetite layer deficient in oxygen, and the crystal lattice constant reaches within a predetermined range.

The above inert gas is not particularly limited, and may be, e.g., nitrogen gas or argon gas. The above reducing gas is also not particularly limited, and may be, e.g., hydrogen gas, natural gas or city gas.

As used herein, the phrase "reducing gas atmosphere" encompasses a mixture of inert gas and reducing gas.

If firing is carried out in an atmosphere containing oxygen without using an inert gas or a reducing gas, it is difficult to obtain high chroma, and also it tends to be difficult to develop interference colors. Even if interference colors are developed, it tends to be difficult to develop interference colors having sufficient significant differences.

The temperature of the above firing is preferably 300° C. or more, and more preferably 300° C. or more and 800° C. or less. If less than 300° C., oxygen deficiency does not occur, and a predetermined lattice constant cannot be obtained. Therefore, it is difficult to obtain high chroma, and also it tends to be difficult to develop interference colors. Even if interference colors are developed, it tends to be difficult to develop interference colors having sufficient significant differences.

On the other hand, if the firing temperature is more than 800° C., the coating iron oxide fine particles will aggregate into particles having large particle diameters, and also aggregation of the coated pigments will occur due to aggregation of coating iron oxide fine particles on the surface of each coated pigment, thus making it impossible to obtain good color development. Also, durability will be reduced by melting of the base itself or by separation of the coating film interface due to thermal expansion.

The duration of the above firing is preferably 5 minutes or more and 24 hours or less, and more preferably 30 minutes or more and 3 hours or less, from when the firing temperature reaches 300° C. Less than 5 minutes is not preferable in that sufficient oxygen deficiency does not occur and a predetermined lattice constant cannot be obtained, and more than 3 hours is not preferable in that productivity decreases. Also, carrying out firing for 24 hours or more is not preferable in that a further change in lattice constant is hardly seen, and aggregation and damage to the coated pigments occur.

Intended Use

By mixing the coated pigments of the present invention into a resin, the mixture can be used as a resin composition having bright interference colors. By applying this composition to sheets such as paper or resin sheets, or to various movables or real estates, coated objects having interference colors are obtained.

Also, by mixing the coated pigments of the present invention into various cosmetic materials, it is possible to obtain coated pigment-containing cosmetic materials having interference colors.

Produced Effects of the Invention

In the present invention, by using the above conditions, especially by setting the crystal lattice constant of the magnetite layer within a specific range, and also combining them with other conditions as necessary, it is possible to obtain the above-described effects of the present invention, i.e., obtain a coated pigment having high chroma and color developing properties, and capable of developing various interference colors such as red-based colors, blue-based colors and yellow-based colors to green-based colors.

The conditions for achieving the crystal lattice constant of the magnetite layer within a specific range, and the above other conditions include, e.g., the thickness of the magnetite layer, the kind of the material of the base layer, the thickness of the light-transmitting material of the base layer and firing conditions (firing temperature, firing duration and firing environment).

EXAMPLES

The present invention is described below using Examples. First, the test method and the raw materials used in each Example are described below.

Test Method

Crystal Lattice Constant

A cell for measurement was uniformly filled with the coated pigments, and the magnetite layers of the coated pigments were identified by an X-ray diffracting device (trade name: "Smart Lab", made by Rigaku Corporation). Measurement was conducted under the following conditions: using CuKα-rays as the X-ray source at a tube voltage of 40 kV, a tube electric current of 30 mA, a sampling width of 0.01° and a scan speed of 0.2°/min. Using the measurement result, "lattice constant refinement" was conducted using integrated powder X-ray analysis software PDXL2, and the lattice constant of the magnetite was calculated.

Color Tone 16.0 g of an acrylic resin binder (Nippe acryl auto clear, made by Nippon Paint Co., Ltd.) was added to 4.0 g of the coated pigments, and they were uniformly mixed together by a planetary stirring defoaming device (Mazel stir KK-400W, made by Kurabo Industries Ltd.), thereby preparing a coating material.

This was applied onto art paper using an applicator having gaps of 100 μm, and was naturally dried at normal temperature, thereby preparing coating films for evaluation.

The color tone was evaluated using an X-Rite MA 681I multi-angle spectrophotometer. The colorimetric values are expressed using the L* a*b* colorimetric system (CIE1976), and colorimetry was conducted by detecting light displaced by 15 degrees from the regular reflection relative to the incident light.

At this time, L* refers to brightness; color a* refers to chromaticity showing hue and chroma on the red-green axis; b* refers to chromaticity showing hue and chroma on the yellow-blue axis; and ΔE refers to the color difference (distance between two points in the L*a* b* color space) between an Example in which the firing step was conducted and a Comparative Example in which the same conditions as used in the Example were used except that the firing step was omitted.

Magnetism 1.0 g of the coated pigments were put into a 50 cc glass beaker, and 10 g of ion-exchanged water was added, thereby preparing a slurry. Next, a ferrite magnet (Φ20 mm, thickness 5 mm, surface magnetic flux density 100 mT) was placed on the outer bottom surface of the beaker, and whether or not the pigments have magnetism was visually checked.

If the coated pigments have no magnetism, no change occurs in the slurry, but if the coated pigments have magnetism, since the coated pigments are magnetically oriented or gathered to the magnet itself, it can be visually confirmed that the pigments have magnetism.

Raw Materials

Base

Flake-shaped aluminum pigments—made by Toyo Aluminum Kabushiki Kaisha, trade name: 5422NS
IPA—Isopropyl Alcohol, made by GODO Co., Ltd.—30% hydrogen peroxide water—made by FUJIFILM Wako Pure Chemical Corporation
Ammonia Water—made by FUJIFILM Wako Pure Chemical Corporation: 25% by mass
Tetraethoxysilane—made by FUJIFILM Wako Pure Chemical Corporation

Magnetite Layer

Polyacrylic acid—made by TOAGOSEI CO., LTD., trade name: Aron T-50
Sodium acetate—made by NICHIWAGOUSEI CO., LTD.
Ferrous Sulfate-7 hydrate—made by ENSHO SANGYO CO., LTD.
Sodium hydroxide—made by FUJIFILM Wako Pure Chemical Corporation

Example 1

Base Producing Step

As the components of each base, commercially available flake-shaped aluminum pigments each formed, on its surface, with a light-transmitting layer composed of silica were used. First, 150 g (in solid content) of the flake-shaped aluminum pigments were put into 1000 g of IPA, and they were stirred and mixed together at 75° C., thereby obtaining a slurry. Then, after adding 30% hydrogen peroxide water into the slurry, and stirring them for 30 minutes, ammonia water and 100 g of ion-exchanged water were added thereto to adjust the pH value of the slurry to 10.0. A solution of 300 g of tetraethoxysilane dissolved in 300 g of IPA was then gradually dropped into the slurry, and the slurry was stirred and mixed at 75° C. for 4 hours. Then, the slurry was subjected to solid-liquid separation, and dried in an oven of 150° C. for 24 hours, thereby obtaining flake-shaped aluminum bases each formed, on its surface, with a light-transmitting layer composed of silica.

Magnetite Layer Producing Step 120 g of the bases obtained above and 1000 g of ion-exchanged water sufficiently degassed with nitrogen were put into a sealed reactor equipped with a stirrer, a pH measuring electrode and a gas introduction tube, and a slurry of which the bases are dispersed in the ion-exchanged water was obtained.

Then, 1.0 g of polyacrylic acid and 7 g of sodium acetate were added to the slurry, and the slurry was heated to 40° C. while stirring the slurry.

Next, an aqueous solution of 110 g of ferrous sulfate-7 hydrate dissolved in 300 g of ion-exchanged water sufficiently degassed with nitrogen was prepared, and, for one hour, this ferrous sulfate aqueous solution was gradually added to the slurry while stirring the slurry. At this time, a 5 wt % sodium hydroxide aqueous solution was added to adjust the pH value to 9. Also, air was introduced into the reactor to adjust the redox potential to −400 mV.

The slurry was then filtered and washed with water, and then, washed with IPA, and dried in an oven at 160° C. for 6 hours, thereby obtaining a magnetite-coated pigment.

Firing Step

By firing 200 g of the above-obtained magnetite-coated pigments in argon gas at 300° C. for 2 hours, the crystal lattice constant of the magnetite was within a predetermine range, and interference color pigments were obtained which show bright pink at the central portion, and red toward the ends. Table 1 shows the measurement results of the color tone, magnetism and crystal lattice constant of the obtained interference color pigments.

Examples 2 to 12, Comparative Examples 2 to 3

Interference color pigments were obtained according to the method described in Example 1 except that the conditions of the steps shown in Table 1 were used. Table 1 shows the measurement results of the color tone, magnetism and crystal lattice constant of the interference color pigments of each example.

Comparative Examples 1, 4 to 6

Coated pigments were prepared in the same manner as in Example 1 except that the conditions of the base producing step and the magnetite producing step shown in Table 1 were used, and the firing step was omitted. Table 1 shows the measurement results of the color tone, magnetism and crystal lattice constant of interference color pigments of each example.

TABLE 1

| | | Base material producing step | Magnetite layer producing step | Firing step | | Measurement - evaluation | | |
| | | Amount of tetraethoxysilane | Amount of base material | Atmos- | Temper- ature | Color tone (light displaced by 15 degrees was detected) | | |
| | | (g) | (g) | sphere | (° C.) | L* | a* | b* |
|---|---|---|---|---|---|---|---|---|
| Example | 1 | 300 | 120 | Argon | 300 | 106.0 | 35.8 | 34.3 |
| | 2 | | | | 350 | 101.9 | 33.6 | 47.6 |
| | 3 | | | | 400 | 102.7 | 27.8 | 56.8 |
| | 4 | | | | 500 | 99.7 | 26.5 | 55.1 |
| | 5 | | | Nitrogen | 300 | 107.8 | 31.3 | 36.2 |
| | 6 | | | | 350 | 105.8 | 26.7 | 56.6 |
| | 7 | | | | 400 | 104.0 | 22.9 | 61.9 |
| | 8 | | | City gas | 300 | 101.4 | 32.4 | 40.8 |
| | 9 | | | Vacuum (*5) | 400 | 98.1 | 29.5 | 44.8 |
| | 10 | 400 | 160 | Argon | 400 | 86.0 | 26.1 | −18.0 |
| | 11 | 300 | | | 400 | 96.6 | 18.1 | 24.5 |
| | 12 | | 240 | | 400 | 123.1 | −7.8 | 58.3 |
| Comparative Example | 1 | 300 | 120 | firing step was omitted | | 113.9 | 27.0 | 24.2 |
| | 2 | | | Argon | 200 | 112.9 | 27.3 | 24.3 |
| | 3 | | | Air | 300 | 112.6 | 27.6 | 24.4 |
| | 4 | 400 | 160 | firing step was omitted | | 122.8 | 2.0 | 4.4 |
| | 5 | 300 | | | | 119.8 | 9.0 | 59.8 |
| | 6 | | 240 | | | 132.6 | −2.0 | 53.6 |

| | | Measurement - evaluation | | | | | |
| | | Color tone (light displaced by 15 degrees was detected) | | Magnetic | Crystal lattice | color | Photo- |
| | | c* | ⊿E | m | constant | (center→side) | graph |
|---|---|---|---|---|---|---|---|
| Example | 1 | 49.5 | 15.5 (*1) | Detected | 8.351 | bright pale red →orange | — |
| | 2 | 58.2 | 27.1 | Detected | 8.375 | bright pale red →orange | — |

TABLE 1-continued

Figure 2:
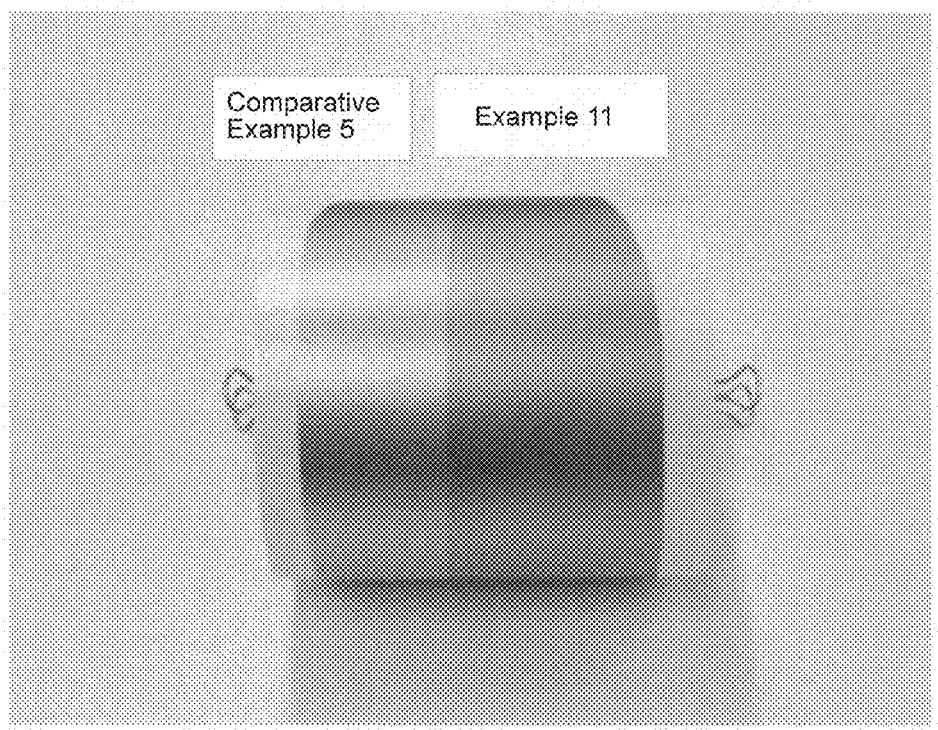
FIG. 2 is a photograph of a sheet which is, after applying thereto coated pigments obtained in Example 11 and coated pigments obtained in Comparative Example 5, rolled into a cylindrical shape.
Figure 3:
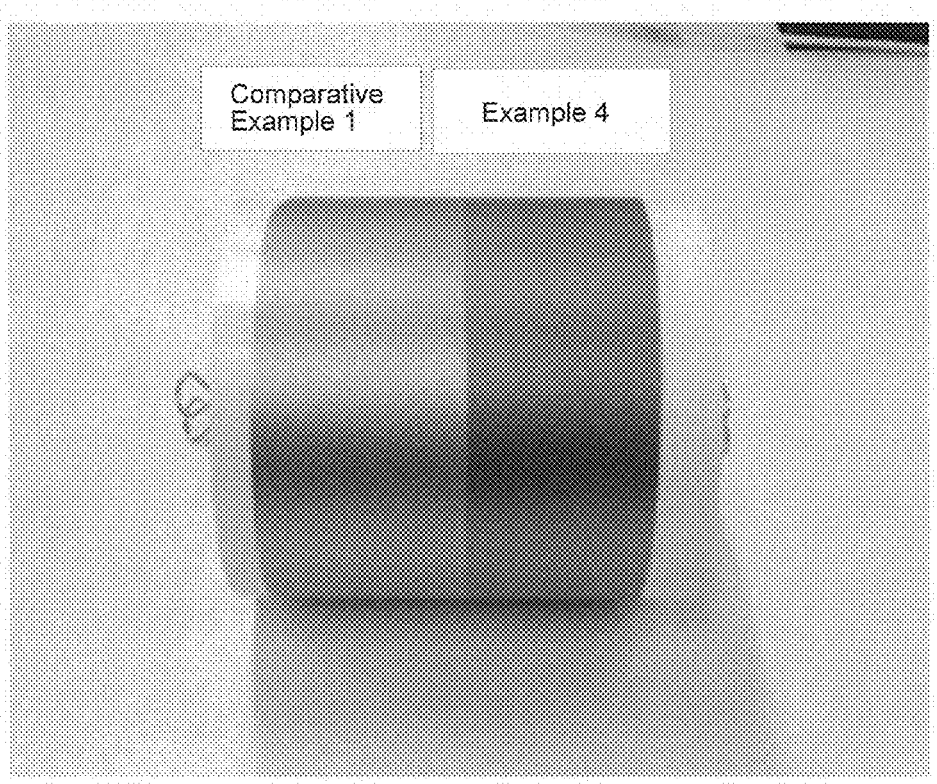
FIG. 3 is a photograph of a sheet which is, after applying thereto coated pigments obtained in Example 4 and coated pigments obtained in Comparative Example 1, rolled into a cylindrical shape.
Figure 4:
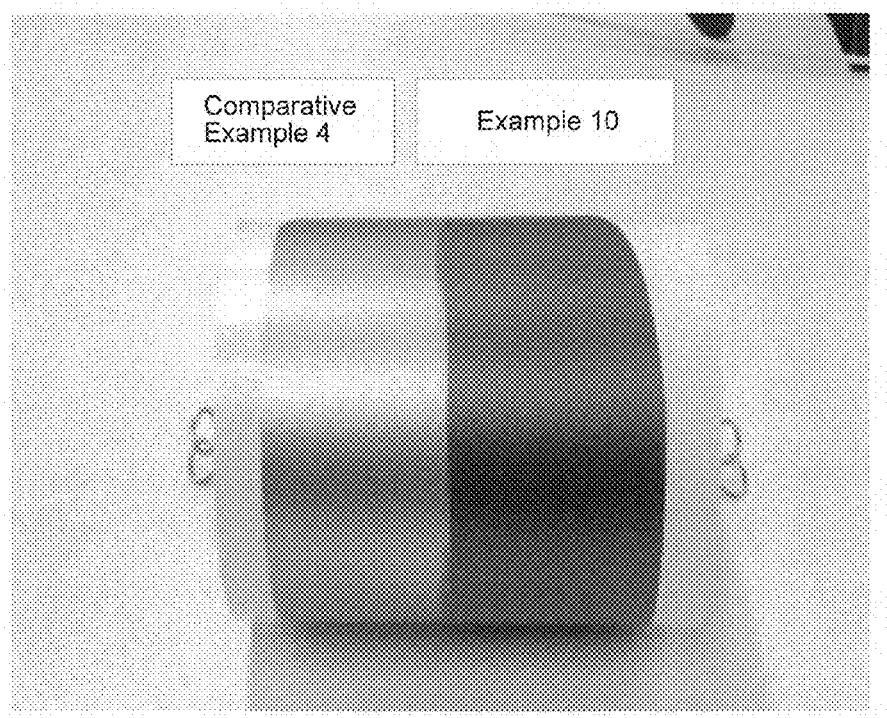
FIG. 4 is a photograph of a sheet which is, after applying thereto, coated pigments obtained in Example 10 and coated pigments obtained in Comparative Example 4, rolled into a cylindrical shape.

|  |  |  |  |  |  |  |  |
|---|---|---|---|---|---|---|---|
|  | 3 | 63.2 | 34.5 |  | Detected | 8.394 | bright red→ orange→green | — |
|  | 4 | 61.2 | 34.1 |  | Detected | 8.398 | bright red→ orange→green | Right side in FIG. 3 |
|  | 5 | 47.9 | 14.2 |  | Defected | 8.367 | bright pale red →orange | — |
|  | 6 | 62.6 | 33.4 |  | Detected | 8.395 | bright pale red →orange | — |
|  | 7 | 65.9 | 39.2 |  | Detected | 8.394 | bright red→ orange→green | — |
|  | 8 | 52.1 | 21.5 |  | Defected | 8.400 | bright red→ orange→green | — |
|  | 9 | 53.6 | 26.1 |  | Detected | 8.369 | bright red→ orange→green | — |
|  | 10 | 31.7 | 49.3 | (*2) | Detected | 8.398 | bright blue→ red purple | Right side in FIG. 4 |
|  | 11 | 30.4 | 43.2 | (*3) | Defected | 8.398 | bright orange→ yellow→green | Right side in FIG. 2 |
|  | 12 | 58.8 | 12.1 | (*4) | Detected | 8.397 | bright yellow →green | Right side in FIG. 1 |
| Comparative Example | 1 | 35.2 | — |  | Detected | 8.345 | pale pink→ pale yellow | Left side in FIG. 3 |
|  | 2 | 35.6 | — |  | Detected | 8.346 | pale pink→ pale yellow | — |
|  | 3 | 36.8 | — |  | Defected | 8.336 | pale pink→ pale yellow | — |
|  | 4 | 4.8 | — |  | Detected | 8.340 | silver | Left side in FIG. 4 |
|  | 5 | 60.5 | — |  | Detected | 8.345 | pale beige →yellow | Left side in FIG. 2 |
|  | 6 | 53.6 | — |  | Detected | 8.344 | pale yellow | Left side in FIG. 1 |

Note:
*1 Color difference by comparison to Comparative Example 1
*2 Color difference by comparison to Comparative Example 4
*3 Color difference by comparison to Comparative Example 5
*4 Color difference by comparison to Comparative Example 6
*5 Vacuum refers to a state depressurized to 1 kPa.
"—" in the Table means "not measured" in the item of color tone, and means, in the item of photograph, that there is no corresponding photograph/drawing.

The above results show that in Examples 1 to 12, which meet the requirements of the present invention, deep interference colors having higher chroma were obtained, whereas in each of Comparative Examples 1 to 6, which do not meet the requirements of the present invention, only light colors having low chroma were obtained, and also interference colors did not occur in some cases.

Also, it became clear that in each of the Examples and the Comparative Examples, since the pigments have magnetism, the magnetite layers have a magnetite structure.

This is apparent from FIGS. 1 to 4, too. FIGS. 1 to 4 show sheets each coated with the interference color pigments obtained in one of Examples and the interference color pigments obtained in one of Comparative Examples, each sheet being rounded into a cylindrical shape, and being placed on an object such that the circumferential surface comes into contact with the object (disposed such that the circumferential direction is the vertical direction in the drawing). Due to such a placement of the sheets, (i) at the central portion, it is possible to observe the hues when seen at substantially right angles relative to the cylindrical surface, and (ii) as the eyeline is moved vertically from the central portion, the angle relative to the cylindrical surface defined by the eyeline decreases, and it is possible to observe the hues when seen with the angle decreased, and thus to check whether the pigments have interference colors.

Example 12 (right) and Comparative Example 6 (left) in FIG. 1 are different from each other in that whether or not the firing step was conducted, and as a result, whether or not the crystal lattice constant is within the predetermined range. In Example 12, the pigments show interference colors from bright yellow (central portion) to bright green (upper and lower portions), i.e., interference colors that are high in chroma and have clear distinctions with respect to a change in hue, whereas in Comparative Example 6, the pigments show light yellow, i.e., not so high in chroma, and it is difficult to see a change in hue between the central portion and the upper and lower portions, that is, no clear interference colors were obtained.

Example 11 (right) and Comparative Example 5 (left) in FIG. 2 are different from each other in that whether or not the firing step was conducted, and whether or not the crystal lattice constant is within the predetermined range. In Example 11, the pigments show interference colors of bright orange at the central portion, and bright yellow to bright green toward the upper and lower portions, i.e., interference colors high in chroma, and having clear distinctions with respect to a change in hue, whereas in Comparative Example 5, the pigments show light beige (central portion) to light yellow (upper and lower portions), thus not so high in chroma, a change in hue between the central portion and the upper and lower portions is seen but not seen clearly, and it is hard to say that clear interference colors were obtained.

Example 4 (right) and Comparative Example 1 (left) in FIG. 3 are different from each other in that whether or not the firing step was conducted, and whether or not the crystal lattice constant is within the predetermined range. In Example 4, the pigments show bright red at the central portion, and bright orange to bright green toward the upper and lower portions, and is high in chroma, and clear interference colors were obtained with respect to a change in hue, whereas in Comparative Example 1, the pigments show light pink at the central portion and light yellow toward the upper and lower portions, but is not so high in chroma, a change in hue between the central portion and the upper and lower portions is seen but not seen clearly, and it is hard to say that clear interference colors were obtained.

Example 10 (right) and Comparative Example 4 (left) in FIG. 4 are different from each other in the conditions of the firing step, and in that whether or not the crystal lattice constant is within the predetermined range. In Example 10, the pigments show bright blue at the central portion, and bright reddish purple toward the upper and lower portions, and is high in chroma, and clear interference colors were obtained with respect to a change in hue, whereas in Comparative Example 4, the entire pigments show silver, and interference colors were not confirmed.

The invention claimed is:

1. A coated object comprising a base object; and a resin composition containing a coated pigment, comprising:
    wherein the coated pigment comprises:
        a base comprising metal flakes coated with a light-transmitting material;
        a magnetite layer coating the base, and having a crystal lattice constant of not less than 8.35 Å; and
        on the magnetite layer, a protective layer composed of any one of a metal hydroxide, a metal oxide hydrate, or a combination thereof.

2. The coated object according to claim 1, wherein the light-transmitting material is at least one selected from the group consisting of silica, alumina, glass, mica and a resin.

3. The coated object according to claim 1, wherein the metal flakes are composed of at least one selected from the group consisting of aluminum, copper, nickel, tin, titanium, zinc, an alloy containing any one or more of these metals, and a stainless steel.

4. A cosmetic material containing the coated object according to claim 1.

5. The coated object according to claim 2, wherein the metal flakes are composed of at least one selected from the group consisting of aluminum, copper, nickel, tin, titanium, zinc, an alloy containing any one or more of these metals, and a stainless steel.

* * * * *